United States Patent
Batzinger et al.

(10) Patent No.: US 9,351,697 B2
(45) Date of Patent: May 31, 2016

(54) METHOD AND SYSTEM FOR DIMENSIONAL ANALYSIS OF AN OBJECT (71) Applicant: General Electric Company, Schenectady, NY (US)

(72) Inventors: Thomas James Batzinger, Burnt Hills, NY (US); Gareth William David Lewis, Greenville, SC (US); Jonathan Matthew Lomas, Simpsonville, SC (US); Christopher Edward Thompson, Greenville, SC (US); Birol Turan, Kocaeli (TR)

(73) Assignee: General Electric Company, Schenectady, NY (US)

(*) Notice: Subject to any disclaimer, the term of this patent is extended or adjusted under 35 U.S.C. 154(b) by 130 days.

(21) Appl. No.: 14/196,260

(22) Filed: Mar. 4, 2014

(65) Prior Publication Data
US 2015/0254817 A1 Sep. 10, 2015

(51) Int. Cl.
*A61B 6/00* (2006.01)
*G01B 9/08* (2006.01)
*G06T 7/00* (2006.01)
*G06T 5/00* (2006.01)
G01B 15/00 (2006.01)
G01B 15/04 (2006.01)
G01B 21/04 (2006.01)
G01B 11/24 (2006.01)

(52) U.S. Cl.
CPC .............. *A61B 6/5247* (2013.01); *A61B 6/4417* (2013.01); *A61B 6/5258* (2013.01);
(Continued)

(58) Field of Classification Search
CPC .......... A61B 6/40; A61B 6/44; A61B 6/4417; A61B 6/52; A61B 6/5211; A61B 6/5229; A61B 6/5247; A61B 6/5258; A61B 6/5282; A61B 6/5294; H04N 3/22; H04N 3/23; H04N 3/233; H04N 3/2335; G06T 3/00; G06T 3/0031; G06T 5/00; G06T 5/006; G06T 7/0024; G06T 7/0051; G06T 7/0057; G06T 7/0065; G06T 9/00; G06T 9/20; G06T 15/00; G06T 15/08; G06T 15/10; G06T 2207/00; G06T 2207/10; G06T 2207/10028; G06T 2207/10072; G06T 2207/10081; G06T 2207/01; G01B 11/00; G01B 11/002; G01B 11/24; G01B 9/00; G01B 9/08
USPC ................ 378/4, 19, 56, 62, 63, 91, 98, 98.3, 378/98.8, 162, 165, 166, 204–206, 210, 378/901; 382/128, 131, 254, 275, 285, 325
See application file for complete search history.

(56) References Cited

U.S. PATENT DOCUMENTS 5,640,436 A * 6/1997 Kawai ................... G06T 11/005
378/4
5,748,768 A * 5/1998 Sivers ..................... G06T 5/006
378/21

(Continued)

OTHER PUBLICATIONS

Soble et al., "Quantitative and Qualitative Evaluation of Geometric Deconvolution of Distortion in Limited-View Computed Tomography," May 1985, pp. 330-335, IEEE Transactions on Biomedical Engineering, vol. BME-32, No. 5.

*Primary Examiner* — Anastasia Midkiff
(74) *Attorney, Agent, or Firm* — Ernest G. Cusick; Hoffman Warnick LLC (57) ABSTRACT

The invention relates generally to the measurement and dimensional analysis of an object and, more particularly, to the correction of distortion in volumetric data of the object using dimensional data of the object. In one embodiment, the invention provides a method of analyzing an object, the method comprising: acquiring volumetric data of an object using an X-ray computed tomography (CT) imaging system; acquiring dimensional data of the object using a vision-based system; determining whether the volumetric data include a distortion; and in the case that the volumetric data are determined to include a distortion, correcting the distortion in the volumetric data using the dimensional data.

20 Claims, 5 Drawing Sheets

(52) U.S. Cl.
CPC .............. *G06T 5/006* (2013.01); *G06T 7/0024* (2013.01); *G06T 7/0065* (2013.01); *G01B 9/08* (2013.01); *G01B 11/24* (2013.01); *G01B 15/00* (2013.01); *G01B 15/04* (2013.01); *G01B 21/045* (2013.01); *G06T 7/0002* (2013.01); *G06T 7/0057* (2013.01); *G06T 2207/10028* (2013.01); *G06T 2207/10081* (2013.01)

(56) References Cited

U.S. PATENT DOCUMENTS

| | | | |
|---|---|---|---|
| 7,215,732 B2 | 5/2007 | Yin et al. | |
| 7,228,254 B2 | 6/2007 | Numata et al. | |
| 7,254,209 B2 | 8/2007 | Zhao et al. | |
| 7,640,137 B2 | 12/2009 | Numata et al. | |
| 7,974,379 B1 | 7/2011 | Case et al. | |
| 8,184,767 B2* | 5/2012 | Mishra | H04N 5/32 378/154 |
| 8,353,628 B1 | 1/2013 | Yun et al. | |
| 2002/0110268 A1* | 8/2002 | Brinker | G06T 5/006 382/131 |
| 2005/0265515 A1* | 12/2005 | Tashiro | A61B 6/032 378/20 |
| 2011/0255763 A1 | 10/2011 | Bogoni et al. | |
| 2013/0009957 A1* | 1/2013 | Arakita | A61B 8/483 345/424 |
| 2013/0249907 A1 | 9/2013 | Humphries et al. | |

* cited by examiner

FIG. 9 ially, an X-ray CT system is employed to obtain volumetric data comprising both external and internal dimensional data. However, when such analyses are carried out on highly contoured objects, it is not uncommon to encounter distortions in the external dimensional data. Such distortions may be caused by X-ray scatter or other X-ray transmission issues. These distortions preclude accurate analysis of either the external or internal features of such objects.

METHOD AND SYSTEM FOR DIMENSIONAL ANALYSIS OF AN OBJECT

BACKGROUND OF THE INVENTION

X-ray computed tomography (CT) has been used to carry out both external and internal dimensional analyses of manufactured objects. In some industries, this technique has become a standard practice for purposes of quality assurance, maintenance, and repair. Typically, an X-ray CT system is employed to obtain volumetric data comprising both external and internal dimensional data. However, when such analyses are carried out on highly contoured objects, it is not uncommon to encounter distortions in the external dimensional data. Such distortions may be caused by X-ray scatter or other X-ray transmission issues. These distortions preclude accurate analysis of either the external or internal features of such objects.

Attempts to correct or accommodate such distortions have employed computer-aided design (CAD) models. Such techniques have had limited success, however, because the analyzed object often varies from that in the CAD model, due to manufacturing issues, wear on the object, etc.

BRIEF DESCRIPTION OF THE INVENTION

In one embodiment, the invention provides a method of analyzing an object, the method comprising: acquiring volumetric data of an object using an X-ray computed tomography (CT) imaging system; acquiring dimensional data of the object using a vision-based system; determining whether the volumetric data include a distortion; and in the case that the volumetric data are determined to include a distortion, correcting the distortion in the volumetric data using the dimensional data.

In another embodiment, the invention provides a system for analyzing an object, the system comprising: an X-ray computed tomography (CT) imaging system; and a vision-based system, wherein the X-ray CT imaging system and the vision based system are configured to simultaneously collect, respectively, volumetric data and dimensional data of an object.

In still another embodiment, the invention provides a computer program product for correcting distortion in volumetric data of an object, the computer program product comprising a computer-readable storage medium having program code embodied therewith, the program code being executable by a computer processor to perform a method comprising: comparing volumetric data of an object with dimensional data of the object; and remapping the volumetric data using the dimensional data, wherein the volumetric data include measurements of both external and internal surfaces of the object and the dimensional data include measurements of external surfaces of the object.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
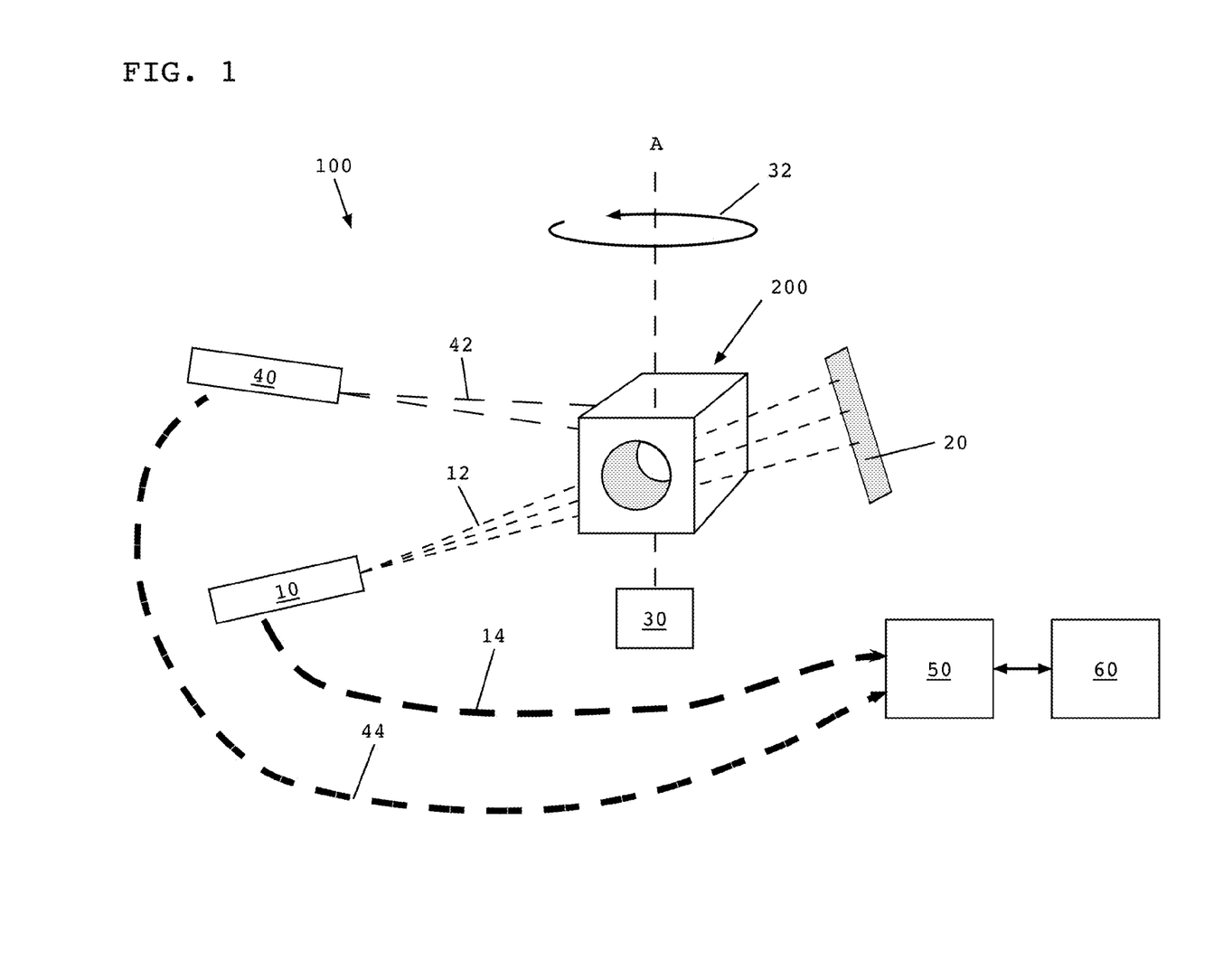
FIG. 1 shows a schematic view of a system according to an embodiment of the invention.

Turning now to the drawings, FIG. 1 shows a schematic view of a system 100 for analyzing an object 200, the system 100 comprising an X-ray transmission device 10 and X-ray receiver 20, as well as a vision-based system 40.

Together, X-ray transmission device 10 and X-ray receiver 20 comprise an X-ray computed tomography (CT) imaging system operable to measure and analyze both external and internal features of object 200. That is, X-ray transmission device 10 and X-ray receiver 20 are operable to measure both absolute and relative features of the external and internal surfaces and feature of object 200, such that the collected measurements, which may be referred to as volumetric data, may be used to construct a three-dimensional model of both exterior and internal features of object 200 suitable for analyzing manufacturing defects, object wear or damage, etc. To do so, X-ray transmission device 10 passes X-rays 12 onto and through object 200, which are received by X-ray receiver 20. The function of such devices and systems are known in the art and would be apparent to one skilled in the art. As such, a detailed explanation of their function will not be provided here for the sake of brevity.

As will be explained in greater detail below, CT imaging systems commonly encounter distortion in the collected volumetric data, such as may be attributable to X-ray scatter or similar phenomena. The correction of such distortion is critical to ensuring the accuracy of any analyses based on or relying upon such volumetric data.

Vision-based system 40 allows for the independent measurement of external features of object 200. That is, vision-based system 40 is operable to measure both absolute and relative features of the external surfaces of object 200, such that the collected measurements, which may be referred to as dimensional data, may be used to construct a three-dimensional model of the exterior features of object 200. Vision-based system 40 may include, for example, a structured light metrology device operable to deliver structured light 42 onto object 200. In some embodiments of the invention, such a structured light metrology device may include a blue light device and/or a white light device. In other embodiments of the invention, vision-based system 40 may include, for example, vision-based coordinate measurement machines, machine vision systems, laser scanners, or camera-based data collection systems, as will be recognized by one skilled in the art.

In operation, X-ray transmission device 10 and vision-based system 40 are each employed to measure features of object 200, collecting volumetric data 14 and dimensional data 44, respectively. According to some embodiments of the invention, volumetric data 14 and dimensional data 44 are collected simultaneously. According to other embodiments of the invention, volumetric data 14 and dimensional data 44 are collected sequentially. Regardless, volumetric data 14 and dimensional data 44 may be delivered to a distortion correction system 50. As will be explained in greater detail below, distortion correction system 50 employs dimensional data 44 to correct distortions that may exist in volumetric data 14. A three-dimensional modeling system 60 may then be employed to construct a three-dimensional model of object 200 using the corrected volumetric data.

System 100 is shown further comprising a manipulating device 30. As is known in the art, object 200 may be rotated 32 about an axis A or otherwise manipulated in three-dimensional space during the collection of volumetric data and/or dimensional data. Although shown in FIG. 1 as rotating 32 object 200 about axis A, it should be understood that manipulating device 30 may manipulate object 200 in other ways, as would be apparent to one skilled in the art.

Figure 2:
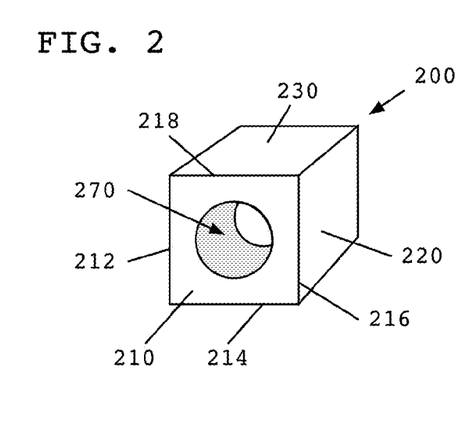
FIGS. 2 and 3 show perspective views of, respectively, an object and a model of the object based on distorted volumetric data.

FIG. 2 shows a perspective view of object 200, a cuboid with a cylindrical passage 270 extending from a first face 210 to an opposite face (obscured). First face 210 includes four edges 212, 214, 216 (adjacent second face 220), 218 (adjacent third face 230).

Figure 3:
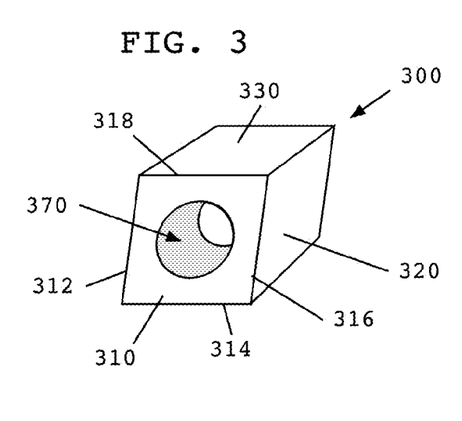

FIG. 3 shows a perspective view of distorted object 300, which has been modeled using distorted volumetric data, for example. As can be seen, edges 312, 314, 316, and 318 do not meet at right angles and cylindrical passage 370 has taken on a slightly ovoid cross-sectional shape, due to the general slanting of distorted object 300. Such distortion may be attributable to X-ray diffraction, for example, during collection of the volumetric data. Features 310, 320, and 330 correspond to first face 210, second face 220, and third face 230, respectively, of FIG. 2.

Figure 4:
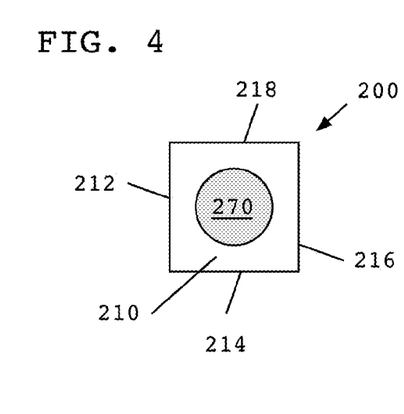
FIGS. 4 and 5 show cross-sectional views of FIGS. 2 and 3, respectively.
Figure 5:
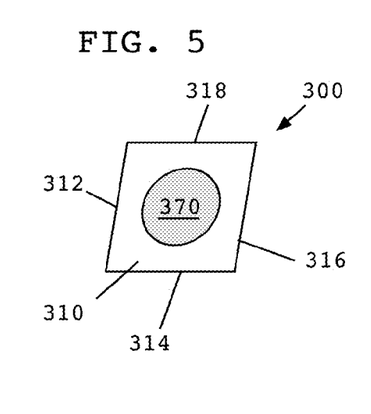
Figure 6:
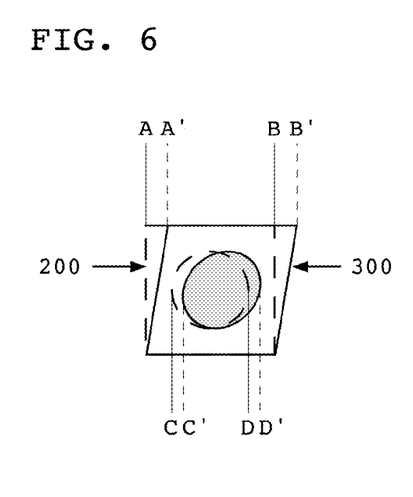
FIG. 6 shows a cross-sectional view of an overlay of FIGS. 4 and 5.

FIGS. 4 and 5 show cross-sectional views of FIGS. 2 and 3, respectively. FIG. 6 shows an overlay of FIGS. 4 and 5, with feature points A, B, C, D of object 200 (shown in phantom) and corresponding distorted points A', B', C', D' of distorted object 300 labeled.

Figure 7:
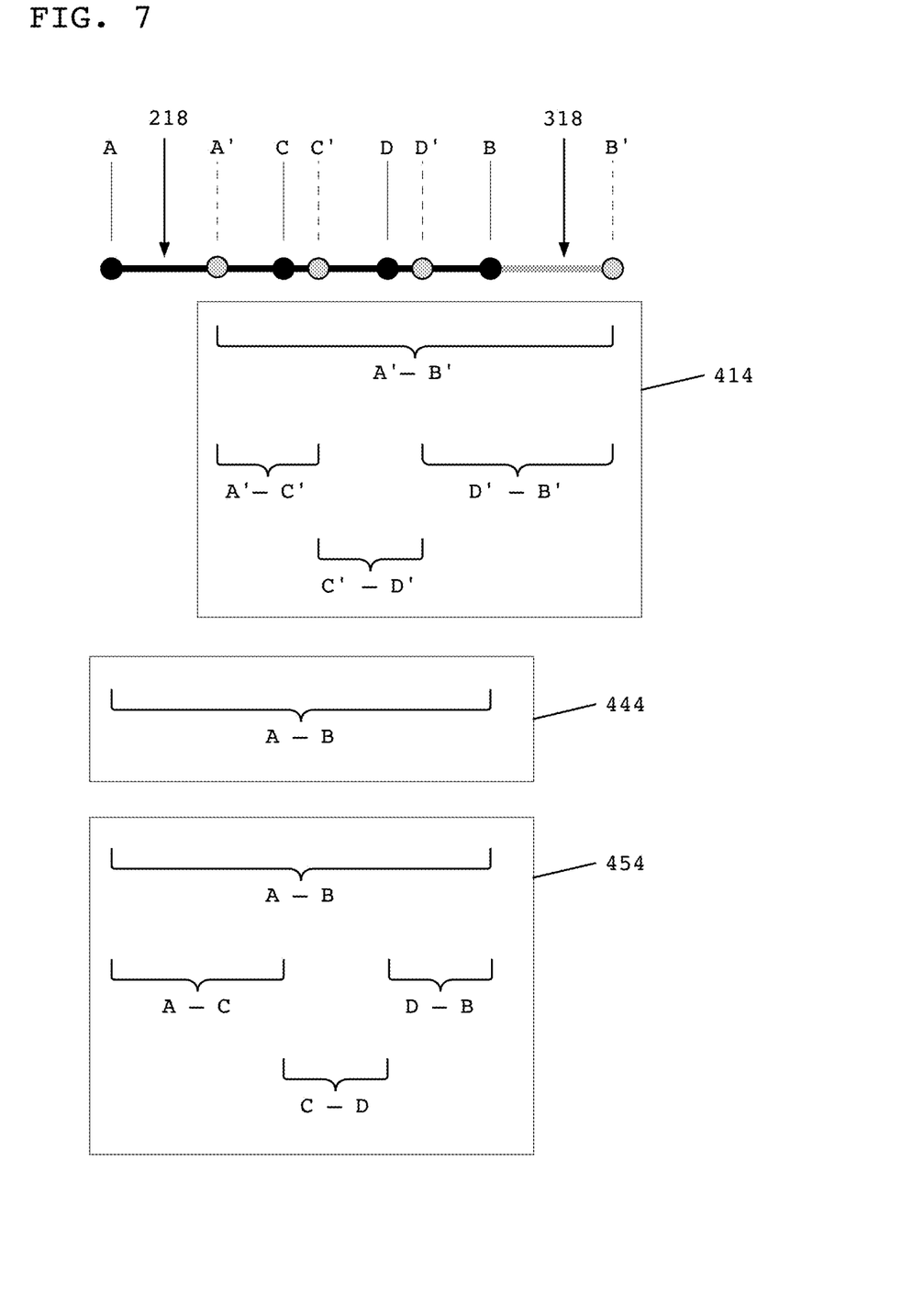
FIG. 7 shows a schematic view of the correction of distorted volumetric data, according to an embodiment of the invention.

FIG. 7 shows a schematic representation of the correction of distorted volumetric data according to an embodiment of the invention. Here, feature points A, B, C, D as may be laid along edge 218 (FIG. 2) and distorted points A', B', C', D' as may be laid along distorted edge 318 (FIG. 3) are shown. The relative distances between various pairs of distorted points A', B', C', D' are shown graphically in distorted volumetric data 414. Without some undistorted reference, there would be no reliable way to correct the distortion seen in distorted volumetric data 414 and no way to accurately model object 200 (FIG. 2) using the volumetric data collected.

However, by using undistorted dimensional data 444, it is possible to correct not only the corresponding external surface features (A' and B') in distorted volumetric data 414, but also internal surface features (C' and D'), for which no undistorted data was collected. This is possible because, similar to the stretching of an elastic band, the distortions typically observed in distorted volumetric data 414 are proportional. That is, the relative distances between distorted data points tend to be proportional to the relative distances between undistorted points of the object being analyzed. As such, it is possible, using dimensional data, which represent only external surfaces of an object, to correct distorted volumetric data representing both external and internal surfaces of the same object. Corrected volumetric data 454 may then be used to accurately model the external and internal surfaces and features of the object.

Various algorithms may be employed in correcting distorted volumetric data 414, as will be apparent to one skilled in the art. Generally, however, such algorithms will rely on the three-dimensional remapping of a distorted volumetric data point (e.g., A') to the same three-dimensional position as that of the corresponding undistorted dimensional data point (e.g., A). This may include, for example, creating a point cloud of object 200 using dimensional data 444, to which at least a portion of the distorted volumetric data 414 are then remapped. Upon remapping two or more such distorted volumetric data points (e.g., A', B'), conventional algorithms may be used to interpolate the corrected three-dimensional positions of intervening distorted volumetric data points (e.g., C', D') for which no corresponding dimensional data point was collected.

As will be appreciated by one skilled in the art, aspects of the present invention may take the form of a computer program product embodied in computer-readable media having computer readable program code embodied thereon.

Any combination of computer-readable media may be utilized. A computer-readable medium may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples of the computer-readable storage medium, while not exhaustive, would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer readable medium that is not a computer readable storage medium and that can communicate, propagate, or transport a program for use by or in connection with an instruction execution system, apparatus, or device.

Program code embodied on a computer-readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, implementation of the functions/acts specified in the flowchart and/or block diagram block or blocks.

These computer program instructions may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 8:
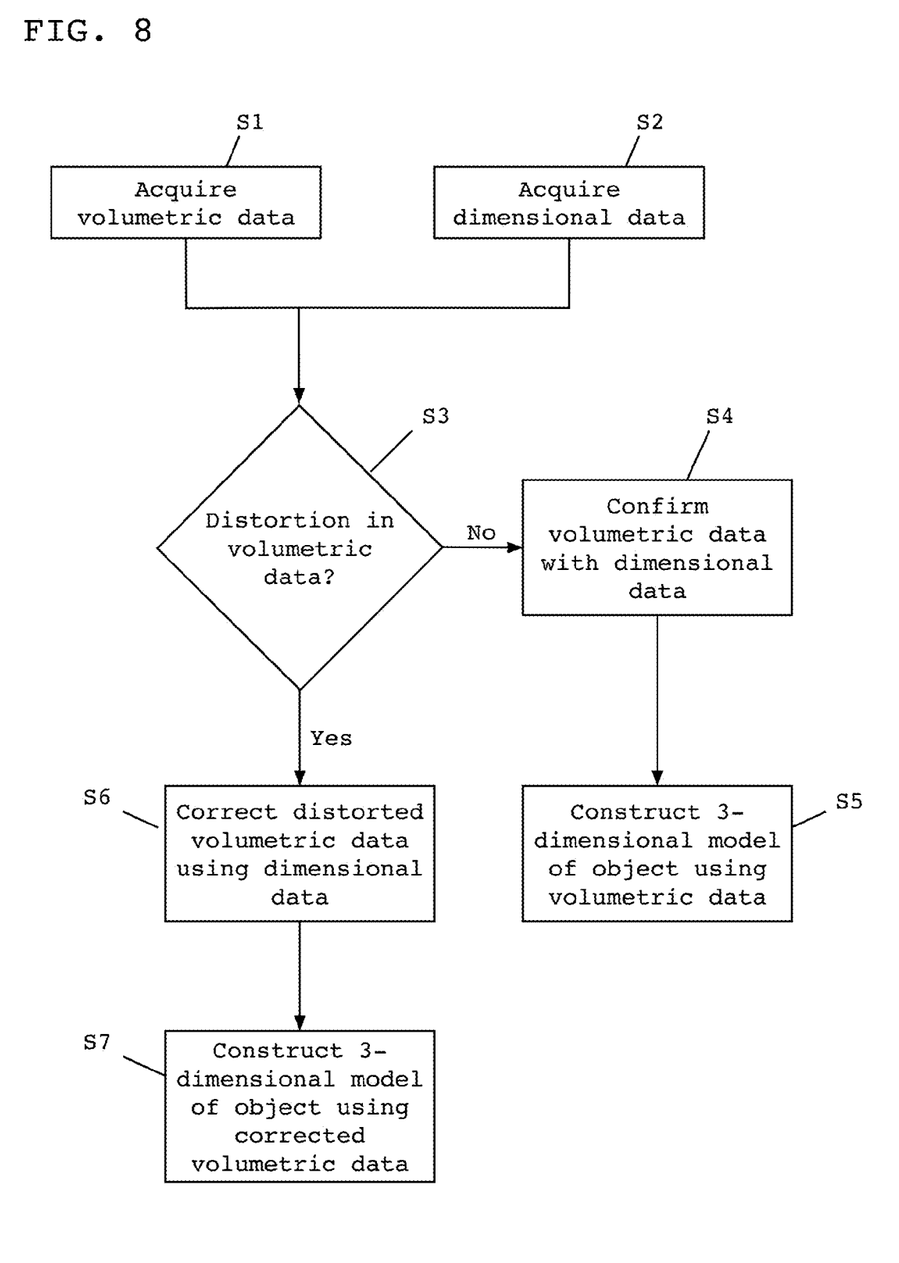
FIG. 8 shows a flow diagram of an illustrative method according to an embodiment of the invention.

FIG. 8 shows a flow diagram of a method according to an embodiment of the invention. At S1, volumetric data of an object are acquired. As noted above, volumetric data include measurements of both external and internal surfaces and features of the object. At S2, dimensional data of the object are acquired, such dimensional data including measurements of external surfaces and features of the object. S1 and S2 may be carried out simultaneously or sequentially.

At S3, it is determined whether distortion exists in the volumetric data collected at S1. Such a determination may be made, for example, by modeling the object using the collected volumetric data and observing distortions or by comparing all or a portion of corresponding three-dimensional points in the volumetric data and the dimensional data. If no distortion is found (i.e., No at S3), the volumetric data may optionally be confirmed at S4 using the dimensional data and, at S5, a three-dimensional model of the object constructed using the volumetric data collected at S1.

If, however, distortion is found in the volumetric data collected at S1 (i.e., Yes at S3), the volumetric data is corrected at S6 using the dimensional data collected at S2, as described above, for example. A three-dimensional model of the object may then be constructed at S7 using the corrected volumetric data from S6.

Figure 9:
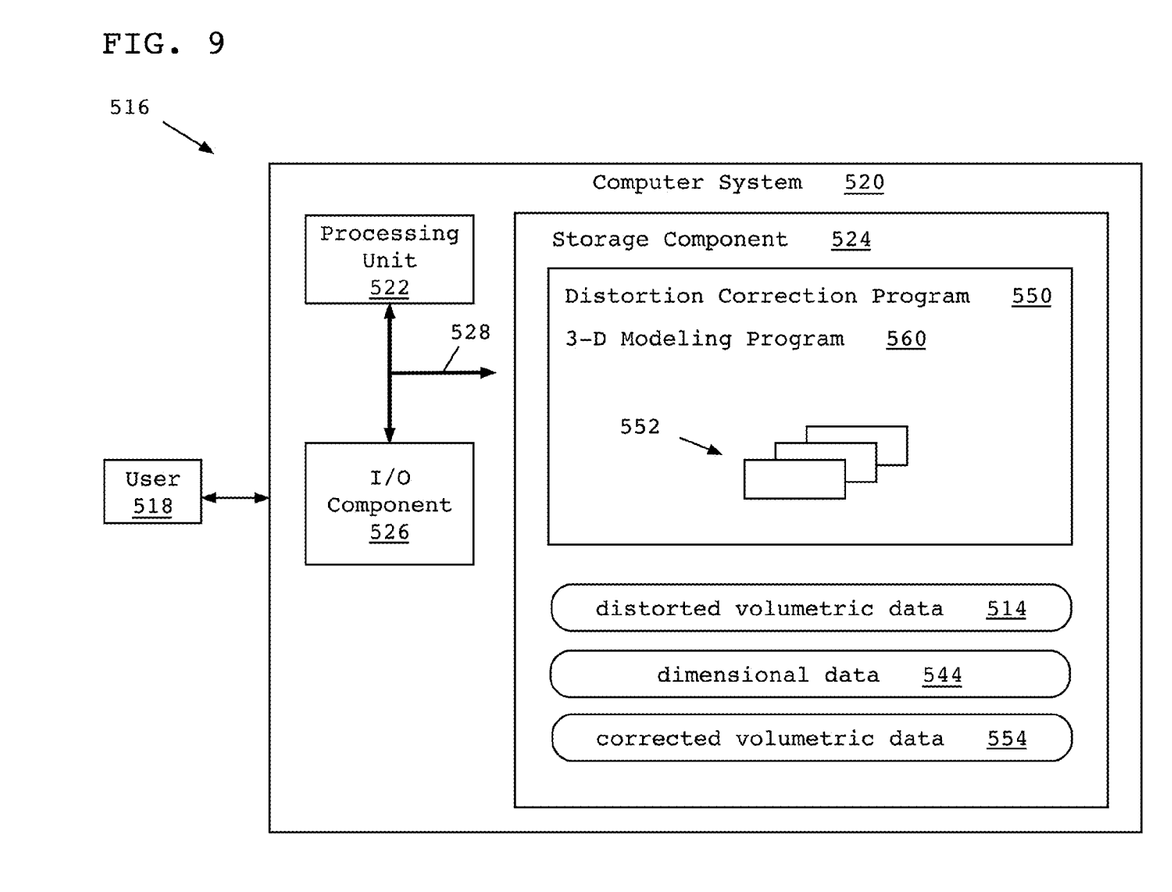
FIG. 9 shows a schematic view of a computer-implemented system for carrying out aspects of the invention, including the correction of distorted volumetric data.

FIG. 9 shows a schematic view of a computer-implemented system 516 for carrying out aspects of the invention, including the correction of distorted volumetric data. To this extent, system 516 includes a computer system 520 that can perform the various process steps described herein for correcting distorted volumetric data. In particular, computer system 520 is shown including a distortion correction program 550 and a 3-D modeling program 560 contained in a storage component 524 of computer system 520.

Computer system 520 is shown including a processing unit 522, storage component 524, which may comprise a memory, input/output (I/O) interfaces 526, and a bus 528. Further, computer system 520 may be in communication with external devices and/or storage systems, as will be apparent to one skilled in the art.

As is known in the art, in general, processing unit 522 executes computer program code, such as distortion correction program 550 or 3-D modeling program 560, that is stored in storage component 524 and/or an external storage system. While executing computer program code, processing unit 522 can read and/or write data from/to storage component 524, an external storage system, and/or I/O interface 526. Bus 528 provides a communication link between each of the components in computer system 520.

In any event, computer system 520 can comprise any general purpose computing article of manufacture capable of executing computer program code installed by a user 518 (e.g., a personal computer, server, handheld device, etc.). However, it is understood that computer system 520 is only representative of various possible computer systems that may perform the various process steps of the invention. Similarly, system 516 is only illustrative of various types of systems for implementing the invention.

As previously mentioned, the distortion correction program 550, when executed, enables the computer system 520 to correct distortion in volumetric data. To this extent, distortion correction program 550 may comprise one or more modules 552 for carrying out the various process steps described above. For example, modules 552 may include, for example, a module for acquiring volumetric data of an object, a module for acquiring dimensional data 554 of an object, a module for determining whether the volumetric data include a distortion (i.e., distorted volumetric data 514), a module for constructing a point cloud using the dimensional data, a module for comparing the volumetric data to the dimensional data, etc.

It is understood that some of the various systems shown in FIG. 9 can be implemented independently, combined, and/or stored in memory for one or more separate computer systems that communicate over a network. Further, it is understood that some of the systems and/or functionality may not be implemented, or additional systems and/or functionality may be included as part of system 516.

The technical effect of carrying out aspects of the invention via a computer-implemented method or system (e.g., by executing program code for correcting distortion in volumetric data using a computer processing unit or processor) is the correction of volumetric data distortion (corrected volumetric data 554), using dimensional data 544, whether such dimensional data are obtained simultaneously with or sequentially to obtaining the distorted volumetric data 514.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of analyzing an object, the method comprising:
    acquiring volumetric data of an object using an X-ray computed tomography (CT) imaging system;
    acquiring dimensional data of the object using a vision-based system;
    determining whether the volumetric data include a distortion; and
    in the case that the volumetric data are determined to include a distortion, correcting the distortion in the volumetric data using the dimensional data.

2. The method of claim 1, wherein the vision-based system includes at least one of the following: a structured light metrology device, a vision-based coordinate measurement machine, a machine vision system, a laser scanner, or a camera-based data collection system.

3. The method of claim 1, further comprising:
    constructing a point cloud using the dimensional data.

4. The method of claim 1, wherein the distortion includes a distortion due to X-ray scatter.

5. The method of claim 1, wherein the volumetric data include measurements of both external and internal surfaces of the object.

6. The method of claim 1, wherein the acquiring steps are carried out simultaneously.

7. The method of claim 1, wherein the acquiring steps are carried out sequentially.

8. The method of claim 1, further comprising:
    constructing a three-dimensional model of the object using the corrected volumetric data.

9. The method of claim 1, further comprising:
    in the case that the volumetric data are determined not to include a distortion, confirming the volumetric data using the dimensional data.

10. The method of claim 1, wherein at least one of acquiring the volumetric data and acquiring the dimensional data includes rotating the object about an axis.

11. A system for analyzing an object, the system comprising:
    an X-ray computed tomography (CT) imaging system; and
    a vision-based system,
        wherein the X-ray CT imaging system and the vision-based system are configured to simultaneously collect, respectively, volumetric data and dimensional data of an object.

12. The system of claim 11, wherein the vision-based system includes at least one of the following: a structured light metrology device, a vision-based coordinate measurement machine, a machine vision system, a laser scanner, or a camera-based data collection system.

13. The system of claim 11, further comprising:
    a distortion correction system operable to correct a distortion in the volumetric data using the dimensional data.

14. The system of claim 13, wherein the distortion is due to X-ray scatter.

15. The system of claim 13, further comprising:
    a three-dimensional modeling system for constructing a three-dimensional model of the object using corrected volumetric data.

16. A computer program product for correcting distortion in volumetric data of an object, the computer program product comprising a computer-readable storage medium having program code embodied therewith, the program code being executable by a computer processor to perform a method comprising:
    comparing volumetric data of an object with dimensional data of the object; and
    remapping the volumetric data using the dimensional data,
        wherein the volumetric data include measurements of both external and internal surfaces of the object and the dimensional data include measurements of external surfaces of the object.

17. The computer program product of claim 16, wherein the method further comprises:
    constructing a point cloud using the dimensional data.

18. The computer program product of claim 17, wherein remapping the volumetric data includes remapping the volumetric data to the point cloud.

19. The computer program product of claim 16, wherein the method further comprises:
    acquiring the volumetric data of the object using an X-ray computed tomography (CT) imaging system; and
    acquiring the dimensional data of the object using a vision-based system.

20. The computer program product of claim 16, wherein the method further comprises:
    constructing a three-dimensional model of the object using the corrected volumetric data.

* * * * *